(12) United States Patent
Åkerblom

(10) Patent No.: US 7,479,789 B2
(45) Date of Patent: Jan. 20, 2009

(54) METHOD AND DEVICE FOR MEASURING THE DEGREE OF FIBER CONCENTRATION

(75) Inventor: Bengt Åkerblom, Vårby (SE)

(73) Assignee: Daprox AB, Skarholmen (SE)

( * ) Notice: Subject to any disclaimer, the term of this patent is extended or adjusted under 35 U.S.C. 154(b) by 0 days.

(21) Appl. No.: 10/590,152

(22) PCT Filed: Feb. 25, 2005

(86) PCT No.: PCT/SE2005/000276

§ 371 (c)(1), (2), (4) Date: Feb. 20, 2007

(87) PCT Pub. No.: WO2005/083408

PCT Pub. Date: Sep. 9, 2005

(65) Prior Publication Data

US 2007/0164757 A1      Jul. 19, 2007

Related U.S. Application Data

(60) Provisional application No. 60/521,145, filed on Feb. 27, 2004.

(30) Foreign Application Priority Data

Feb. 27, 2004    (SE) .................................... 0400491

(51) Int. Cl.
*G01R 27/26* (2006.01)
(52) U.S. Cl. .................. 324/663; 324/666; 162/198
(58) Field of Classification Search ................ 324/664, 324/694
See application file for complete search history.

(56) References Cited

U.S. PATENT DOCUMENTS 2,966,628 A * 12/1960 Bosch .................... 324/666

(Continued)

FOREIGN PATENT DOCUMENTS

DE      27 42 229 A1     3/1979

(Continued)

OTHER PUBLICATIONS

International Search Report dated May 23, 2005.
Written Opinion of the International Searching Authority.

*Primary Examiner*—Diego Gutierrez
*Assistant Examiner*—Benjamin M Baldridge
(74) *Attorney, Agent, or Firm*—Buchanan Ingersoll & Rooney PC

(57) ABSTRACT

A method for measuring the degree of fiber concentration in a pulp in a machine, in particular a refiner for the manufacture of paper pulp, which machine includes a stator and an opposing rotor, which form a grinding gap for the pulp. The stator is provided with at least one sensor device, designed to interact with a rotor surface and including an impedance meter body with a sensor surface which impedance meter body is mounted in the stator in such a way that it can move axially. Measurements of the impedance between the rotor surface and the sensor surface are carried out during an axial movement of the impedance meter body and the measured impedance differences are utilized together with the size of the movement to determine the dielectric constant of the pulp, from which the degree of fiber concentration in the pulp is derivved.

12 Claims, 1 Drawing Sheet

U.S. PATENT DOCUMENTS 4,171,916 A     10/1979   Simms et al.
5,632,881 A      5/1997   Gabelich et al.
5,853,543 A * 12/1998   Hu et al. ..................... 162/198
6,087,837 A      7/2000   Chase

FOREIGN PATENT DOCUMENTS

WO    86/07458 A1   12/1986
WO    03/065028 A1   8/2003

* cited by examiner

METHOD AND DEVICE FOR MEASURING THE DEGREE OF FIBER CONCENTRATION

TECHNICAL FIELD

The present invention relates to a method and device for measuring the degree of fibre concentration in a pulp in a machine, in particular a refiner for the manufacture of paper pulp.

BACKGROUND ART

In the manufacture of paper pulp, it is important to know the degree of fibre concentration in the paper pulp, as this determines the characteristics of the finished product. It is therefore customary, in a refiner designed for the manufacture of paper pulp, to utilize optical concentration meters for this purpose, arranged in a blow line coming out from the refiner.

Such a method is described in WO 86/07458, in which at least two optical concentration meters are used which shine through the finished paper pulp with infrared and polarized light respectively, and thereafter measure the absorption and reflection of the light and the de-polarizing effect respectively. The measurement results are then used to calculate the degree of fibre concentration in the paper pulp.

U.S. Pat. No. 4,171,916 also describes a method in which polarization, absorption and reflection of the transmitted light are used to determine the degree of fibre concentration in the paper pulp.

These methods work relatively well provided that the degree of fibre concentration is not too high, preferably below approximately 5% by volume, but are less applicable for paper pulps with a higher degree of fibre concentration. As, in certain cases, it is desirable to achieve a degree of fibre concentration of upwards of 30% by volume, it is desirable to produce a method and a device that can produce results that are reliable even at such high degrees of fibre concentration.

OBJECT OF THE INVENTION

The object of the present invention is to provide a method and a device for measuring the degree of fibre concentration in a pulp, which give reliable results even at high values of said degree of fibre concentration.

DISCLOSURE OF INVENTION

The object is achieved by a method and a sensor device according to the embodiments of the present invention.

An embodiment relates to a method for measuring the degree of fibre concentration in a pulp inside a machine, in particular a refiner for the manufacture of paper pulp, which machine comprises a stator and an opposing rotor, which form a grinding gap for the pulp. The stator is provided with at least one sensor device, designed to interact with a rotor surface and comprising an impedance meter body with a sensor surface, which impedance meter body is mounted in the stator in such a way that it can move axially. The method is characterized in that measurements of the impedance between the rotor surface and the sensor surface are carried out during an axial movement of the impedance meter body and in that the measured impedance differences are utilized together with the size of the movement to determine the dielectric constant of the pulp, from which the degree of fibre concentration in the pulp is derived.

By utilizing the impedance for calculating the degree of fibre concentration, instead of optical methods, a method is achieved with a degree of reliability that is independent of the values of the degree of fibre concentration.

The size of the movement is advantageously measured using a measurement device that communicates with the impedance meter body, which makes it possible to adjust the size of the movement in accordance with the size of the grinding gap.

In addition, it is advantageous also to measure the size of the grinding gap and to utilize this value in determining the dielectric constant of the pulp, by means of which an even higher degree of reliability is achieved.

Another embodiment relates to a sensor device for measuring the degree of fibre concentration in a pulp inside a machine, in particular a refiner for the manufacture of paper pulp, which machine comprises a stator and an opposing rotor, which form a grinding gap for the pulp. The sensor device is designed to be mounted in the stator to interact with a rotor surface and comprises an impedance meter body with a sensor surface, which impedance meter body is movable in an axial direction and is connected to an operating mechanism for axial movement relative to the housing. The sensor device is characterized in that the impedance meter body is arranged to measure the impedance between the sensor surface and the rotor surface during axial movement thereof.

By utilizing the impedance for calculating the degree of fibre concentration, a sensor device is obtained with reliability that is independent of the values of the degree of fibre concentration.

It is advantageous if essentially the whole of the impedance meter body is clad with an insulating material, as by this means leakage flows that can affect the result are reduced and the reliability of the sensor device is thus improved.

As mentioned above, it is advantageous if the sensor device comprises a measuring device that communicates with the impedance meter body, for measuring the axial movement of the impedance meter body.

It is also advantageous if the impedance meter body is also arranged to measure the size of the grinding gap, as taking this factor into account increases the reliability of the sensor device and, by letting the impedance sensor body carry out this measurement, a compact sensor device is achieved.

Finally, it is also advantageous if the sensor device comprises a separate distance meter body, separate from the impedance meter body and arranged to measure the size of the grinding gap, as it is thereby possible to utilize existing distance meter bodies for this function so that the impedance meter body is less complicated and therefore cheaper to manufacture.

BRIEF DESCRIPTION OF DRAWINGS

The invention will now be described with reference to the attached drawings in which.

MODE(S) FOR CARRYING OUT THE INVENTION

Figure 1:
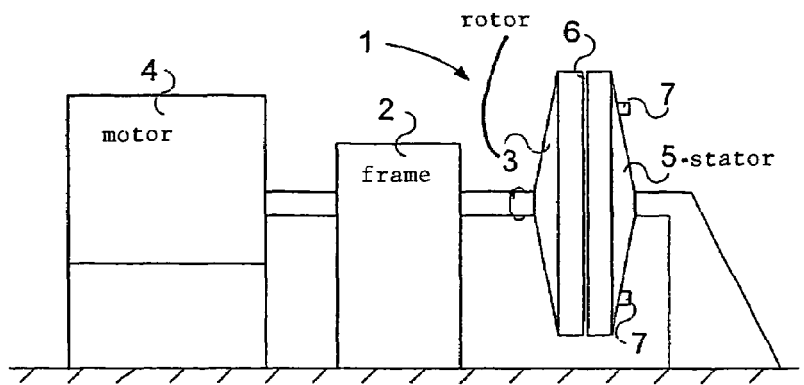
FIG. 1 shows a side view of a refiner with a sensor device according to a preferred embodiment of the present invention.

FIG. 1 shows schematically a machine 1 of the refiner type designed for the manufacture of paper pulp. The refiner 1 comprises a rotor 3 mounted in a frame 2 in such a way that it can move, which rotor 3 is earthed via an earth lead 33 (see FIG. 2), is driven by means of a motor 4 and can be moved axially in a direction towards and away from the stator 5 for adjusting the size of a grinding gap 6 between the rotor 3 and the stator 5 in which grinding of the paper pulp takes place. The refiner 1 is also provided with two sensor devices 7 according to the present invention, for measuring the degree of fibre concentration in the paper pulp, and an inlet (not shown) and a blow line (not shown) for the input and removal of the paper pulp.

Figure 2:
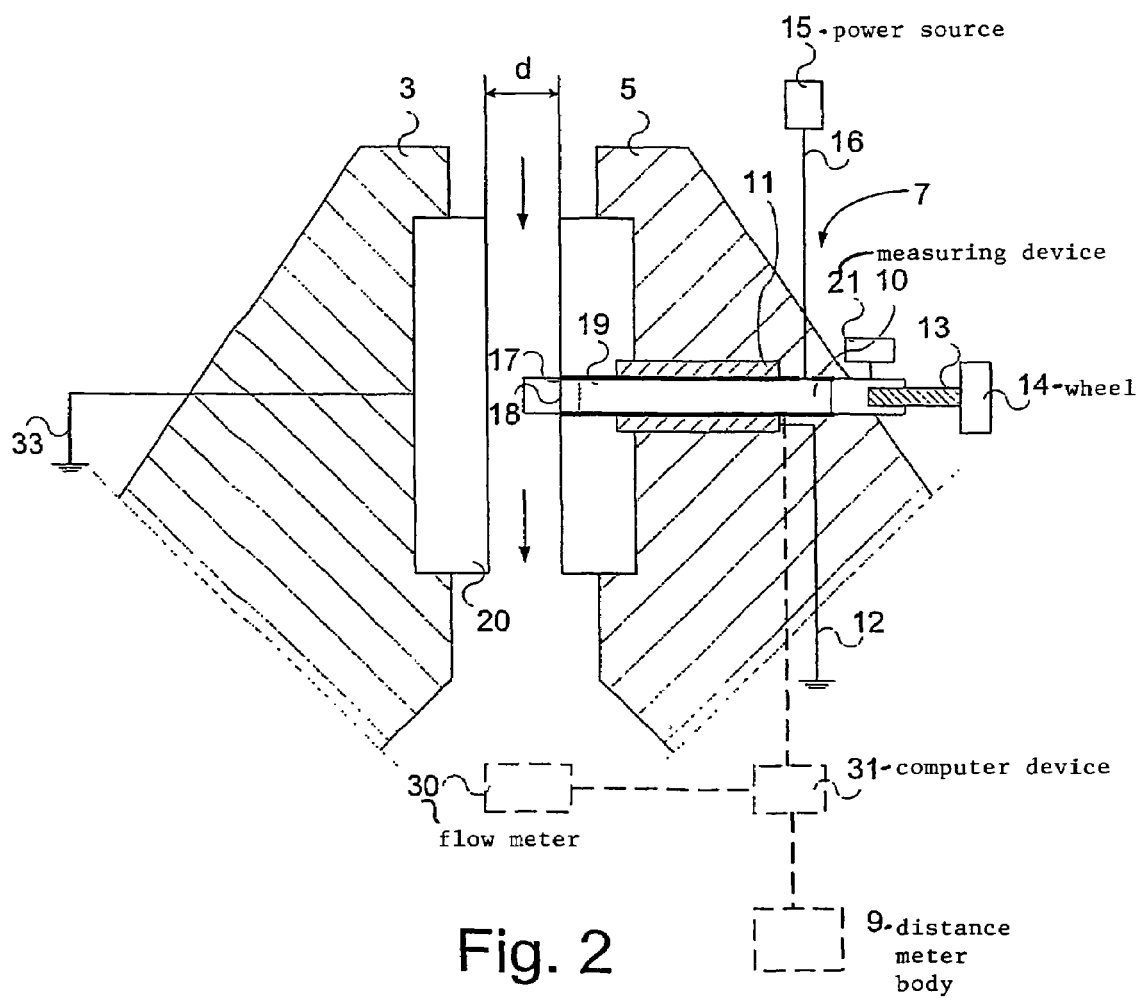
FIG. 2 shows a detailed view of the sensor device according to FIG. 1.

As shown in greater detail in FIG. 2, both the rotor 3 and the stator 5 are provided with grinding segments 20 that have a suitable surface for grinding paper pulp and are arranged in a suitable number in a ring on the stator 5 and rotor 3. These grinding segments 20 are subject to wear when in use and are therefore suitably arranged to be replaceable. As shown in FIG. 2, each sensor device 7 comprises a housing 11 permanently mounted in the stator 5, for example screwed into a hole in the stator, in which an impedance meter body 10 is arranged in such a way that it can move axially. The housing 11 is earthed via an earth lead 12. The axial movement of the impedance meter body 10 is achieved by the operation of an operating mechanism 13, here in the form of a roller screw. The roller screw 13 has a suitably fine pitch and is attached to the rear end of the impedance meter body 10 in such a way that a revolution of the roller screw 13 results in a movement thereof in an axial direction. The operation of the roller screw 13 can, for example, be carried out by means of a wheel 14, but it is also possible to use other operating devices, for example, comprising an electric stepping motor or a servo motor, by means of which operation can be carried out at a distance from the stator 5. The impedance meter body 10 is connected to a power source 15 via a lead 16 and is also advantageously clad externally with an insulating material 19 over essentially all its surface, with the exception primarily of a sensor surface 18 located at the front. The insulating material 19 can, for example, consist of a layer of paint, a Teflon hose, plastic tube or the like, and its task is to reduce leakage flows and thereby minimize their effect on the impedance measurements.

Before the sensor device 7 in FIG. 2 is put into use, calibration measurements are carried out in which a correlation is established between the dielectric constant of the pulp and the degree of fibre concentration in the said pulp, which is possible as the dielectric constant depends on the water content in the pulp, which in turn is associated with the said degree of fibre concentration. Thereafter, measurements are carried out of the impedance between a rotor surface (here a grinding segment surface), and the sensor surface 18, preferably at one or more frequencies within a range of 100 Hz-100 kHz, while moving the impedance meter body 10 in an axial direction towards and away from the rotor 3. The size of the movement is measured here by a measuring device 21 that is in communication with the impedance meter body 10, but can alternatively assume a predetermined value or can be calculated from the number of revolutions of the roller screw that have been carried out. With knowledge of the size of the movement of the impedance sensor body 10 and the change in the impedance over the said movement, a value for the dielectric constant of the pulp can be determined, after which the abovementioned correlation between the dielectric constant and the degree of fibre concentration is utilized to determine the said degree of fibre concentration for the pulp. The calculations of the degree of fibre concentration have been carried out here by a computer device 31 connected to the sensor device, but can, of course, also be carried out manually.

It is possible that, in certain cases, the distance d between the grinding segments 20 on the rotor 3 and the stator 5 affects the measurements, as this distance d determines the fineness of the pulp, that is the size of the fibres (a reduction in the distance results in smaller fibre sizes). It is therefore possible to let a distance meter body 9 measure this distance d, which distance meter body 9 is arranged separately relative to the impedance meter body 10 and is advantageously of the AGS type according to, for example, the Swedish patent SE 520 322 or the Swedish patent application no. 0300794-5, and is connected to the computer device 31, or alternatively it is possible for the impedance meter body and the abovementioned distance meter body to constitute an integrated unit that carries out both the impedance measurement and the distance measurement.

Finally, it can be advantageous if the sensor device comprises a flow meter, here shown schematically by 30, for measuring the flow of the pulp, advantageously either located in the inlet or the blow line, and also connected to the computer device 31.

By means of a device and a method as described above, it is possible to measure the degree of fibre concentration for the pulp in the grinding gap, even when this assumes values around 30% by volume, as the method is not dependent upon the transparency of the pulp.

It will be obvious to experts within the field that the invention described above can be modified within the framework of the scope of the patent claims. For example, the refiner can be provided with one sensor device or more than two sensor devices, comprising any number of impedance meter bodies or distance meter bodies that can be located anywhere in the stator. In addition, the roller screw 13 can be replaced by a different mechanism, for example a hydraulic or pneumatic mechanism.

The invention claimed is:

1. Method for measuring the degree of fiber concentration in a pulp inside a machine, in particular a refiner for the manufacture of paper pulp, which machine comprises a stator and an opposing rotor, which form a grinding gap for the pulp, with the stator being provided with at least one sensor device, designed to interact with a rotor surface and comprising an impedance meter body with a sensor surface, which impedance meter body is mounted in the stator in such a way that it can move axially, wherein measurements of the impedance between the rotor surface and the sensor surface are carried out during an axial movement of the impedance meter body and wherein the measured inpedance differences are utilized together with the size of the movement to determine the dielectric constant of the pulp, from which the degree of fiber concentration of the pulp is derived.

2. Method for measuring the degree of fiber concentration according to claim 1, wherein the size of the movement is measured using a measurement device that communicates with the impedance meter body.

3. Method for measuring the degree of fiber concentration according to claim 1, wherein the size of the grinding gap is also measured and the value of this is utilized in determining the dielectric constant of the pulp.

4. Sensor device for measuring the degree of fiber concentration in a pulp inside a machine, in particular a refiner for the manufacture of paper pulp, which machine comprises a stator and an opposing rotor, which form a grinding gap for the pulp, which sensor device is designed to be mounted in the stator to interact with a rotor surface and comprises an impedance meter body with a sensor surface, which impedance meter body is movable in an axial direction and is connected to an operating mechanism for axial movement relative to the housing, wherein the impedance meter body is arranged to measure the impedance between the sensor surface and the rotor surface during axial movement thereof and wherein the measured impedance differences are utilized together with the size of the movement of the impedance meter body to determine the degree of fiber concentration in the pulp.

5. Sensor device according to claim 4, wherein essentially the whole of the impedance meter body is clad with an insulating material.

6. Method for measuring the degree of fiber concentration according to claim 3, wherein a measuring device communicates with the impedance meter body for measuring the axial movement thereof.

7. Sensor device according to claim 5, wherein the impedance meter body is also arranged to measure the size of the grinding gap.

8. Sensor device according to claim 5, wherein the sensor device also comprises a distance meter body, separate from the impedance meter body and arranged to measure the size of the grinding gap.

9. Method for measuring the degree of fiber concentration according to claim 2, wherein the size of the grinding gap is also measured and the value of this is utilized in determining the dielectric constant of the pulp.

10. Sensor device according to claim 4, wherein a measuring device communicates with the impedance meter body for measuring the axial movement thereof.

11. Method for measuring the degree of fiber concentration according to claim 6, wherein the impedance meter body is also arranged to measure the size of the grinding gap.

12. Method for measuring the degree of fiber concentration according to claim 6, wherein the sensor device also comprises a distance meter body, separate from the impedance meter body and arranged to measure to size of the grinding gap.

* * * * *